United States Patent [19]

Hansen et al.

[11] Patent Number: 4,556,740
[45] Date of Patent: Dec. 3, 1985

[54] PHOSPHORUS COMPOUNDS

[75] Inventors: Hans-Jürgen Hansen, Riehen; Rudolf Schmid, Basle, both of Switzerland

[73] Assignee: Hoffmann-La Roche Inc., Nutley, N.J.

[21] Appl. No.: 524,714

[22] Filed: Aug. 19, 1983

[30] Foreign Application Priority Data

Aug. 27, 1982 [CH] Switzerland .......................... 5109/82
Jul. 1, 1983 [CH] Switzerland .......................... 3641/83

[51] Int. Cl.[4] .......................... C07F 9/50; C07F 9/52
[52] U.S. Cl. .......................... 568/13; 568/17
[58] Field of Search .......................... 568/17, 13

[56] References Cited

U.S. PATENT DOCUMENTS 3,064,055 11/1962 Herring .................................. 568/17
3,798,241 3/1974 Kagan et al. ...................... 260/340.9
4,123,465 10/1978 Valentine .............................. 568/13
4,356,324 10/1982 Bergstein et al. ...................... 568/17

OTHER PUBLICATIONS

Chemical Abstracts 94 65844p (1981).
Kosolapoff, Organic Phosphorus Cpd. Wiley N.Y. VI, p. 209 (1972).
Chemical Abstracts 97 92408t (1982).
Chemical Abstracts 94 121896w (1981).
Chemical Abstracts 97 109322k (1982).

*Primary Examiner*—Helen M. S. Sneed
*Attorney, Agent, or Firm*—Jon S. Saxe; Bernard S. Leon

[57] ABSTRACT

Novel chiral phosphorus compounds of the general formula

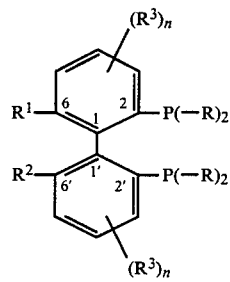

wherein R signifies substituted or unsubstituted phenyl, $R^1$ and $R^2$, which can be the same or different, signify hydrogen, lower alkyl, lower alkoxy, di-lower alkylamino or protected hydroxymethyl or $R^1$ and $R^2$ together signify the group

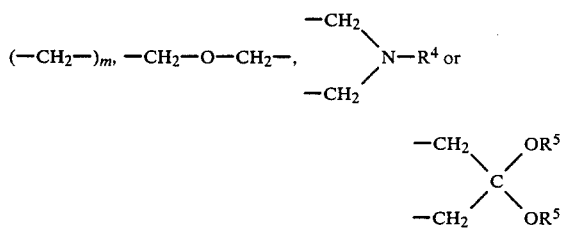

in which m represents a number 3 to 5, $R^4$ represents lower alkyl, substituted or unsubstituted phenyl or benzyl and $R^5$ represents lower alkyl or both $R^5$'s together represent lower alkylene, $R^3$ signifies methyl, lower alkoxy, di-lower alkylamino or fluorine and n signifies the number 0, 1, 2 or 3, are described.

The compounds of formula I are useful in the form of complexes with a metal of Group VIII as catalysts for asymmetric hydrogenations and enantioselective hydrogen displacements in prochiral allylic systems.

4 Claims, No Drawings

PHOSPHORUS COMPOUNDS

The present invention is concerned with novel chiral phosphorus compounds, present in the (R)- or (S)-form, of the formula

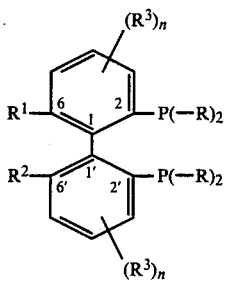

wherein R is substituted or unsubstituted phenyl, $R^1$ and $R^2$, which can be the same or different, are hydrogen, lower alkyl, lower alkoxy, di-lower alkylamino or protected hydroxymethyl or $R^1$ and $R^2$ together are the group

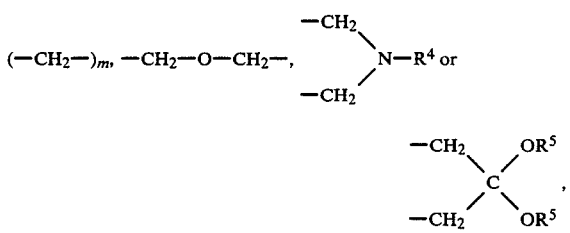

in which m is the integer 3, 4 or 5, $R^4$ represents lower alkyl, substituted or unsubstituted phenyl or benzyl and $R^5$ is lower alkyl or both $R^5$ moieties together represent lower alkylene, $R^3$ is methyl, lower alkoxy, di-lower alkylamino or fluorine and n is the integer 0, 1, 2 or 3.

The invention is also concerned with the manufacture of the phosphorus compounds of formula I and their use for asymmetric hydrogenations or for enantioselective hydrogen displacements in prochiral allylic systems.

In the scope of the present invention, the aforementioned phenyl and benzyl groups can be not only unsubstituted, but also substituted in the ortho, meta or para position or also multiply substituted. As substituents there come into consideration lower alkyl or lower alkoxy groups, preferably methyl or methoxy groups, di-lower alkylamino groups, preferably dimethylamino groups, and fluorine. The term "lower alkyl" means in the scope of the present invention straight-chain or branched-chain alkyl groups containing 1 to 4 carbon atoms such as methyl, ethyl, propyl, isopropyl, n-butyl, isobutyl and tert.butyl. The terms "lower alkoxy" and "di-lower alkylamino" mean groups in which the alkyl moiety has the foregoing definition The term "lower alkylene" means dimethylene or trimethylene. As protecting groups for the hydroxymethyl group there come into consideration in the scope of the present invention especially the customary ether-forming groups such as, for example, benzyl, methyl, tert.butyl, methoxymethyl and the like, and ester-forming groups such as, for example, acetyl, benzoyl and the like.

Under the term "leaving group" used hereinafter there are to be understood in the scope of the present invention groups such as, for example, halogen, especially chlorine and bromine, and alkoxy groups such as methoxy and the like.

Preferred phosphorus compounds of formula I above are those in which R is unsubstituted phenyl or phenyl substituted with methyl or fluorine, $R^1$ and $R^2$ are the same and are lower alkyl or $R^1$ and $R^2$ together are the group —$CH_2$—O—$CH_2$—, n is the integer 0 or 1 and $R^3$ is methyl, fluorine or di-lower alkylamino. When n is the integer 1, the substituent $R^3$ is preferably situated in the m-position to the phosphorus.

The following are examples of preferred compounds of formula I:

(R)- or (S)-(6,6'-dimethyl-2,2'-biphenylylene)-bis-(diphenylphosphine), (R)- or (S)-(4,4',6,6'-tetramethyl-2,2'-biphenylylene)-bis(diphenylphosphine), (R)- or (S)-(3,3',6,6'-tetramethyl-2,2'-biphenylylene)-bis(diphenylphosphine), (R)- or (S)-(4,4'-bis(dimethylamino)-6,6'-dimethyl-2,2'-biphenylylene)-bis(diphenylphosphine), (R)- or (S)-(4,4'-difluoro-6,6'-dimethyl-2,2'-biphenylylene)-bis(diphenylphosphine), (R)- or (S)-(6,6'-dimethyl-2,2'-biphenylylene)-bis(di-p-tolylphosphine), (R)- or (S)-(6,6'-dimethyl-2,2'-biphenylylene)-bis(di-o-tolylphosphine), (R)- or (S)-(6,6'-dimethyl-2,2'-biphenylylene)-bis(di-m-fluorophenylphosphine), (R) or (S)-1,11-bis(diphenylphosphino)-5,7-dihydrodibenz[c,e]oxepin.

The compounds of formula I in accordance with the invention can be manufactured by (a) reacting a racemic or optically active compound of the formula

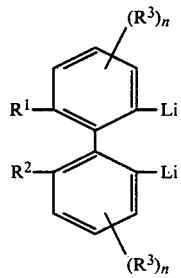

wherein $R^1$, $R^2$, $R^3$ and n are defined as above, with a compound of the formula

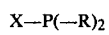

wherein R is defined as above and X is a leaving group, or (b) reacting a racemic or optically active compound of formula II with a compound of the formula

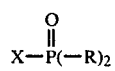

wherein R and X are defined as above, and reducing the thus-obtained compound of the formula

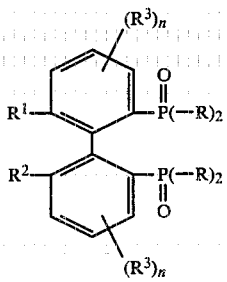

wherein R, R¹, R², R³ and n are defined as above, and, if necessary, resolving a racemic compound of formula I obtained into the optical antipodes.

The reaction of a compound of formula II with a compound of formula III can be carried out in a manner known per se. The reaction is conveniently carried out in an inert aprotic organic solvent such as, for example, an ether (e.g. diethyl ether, tetrahydrofuran, dimethoxyethane and the like). The reaction is also conveniently carried out at a temperature from about room temperature to about $-120°$ C., preferably below about $-60°$ C. and especially below about $-90°$ C. The pressure is not critical and the reaction can be carried out readily at atmospheric pressure.

The reaction of a compound of formula II with a compound of formula IV can be carried out in a manner analogous to the reaction described previously.

The reduction of a compound of formula V can be carried out in a manner known per se. Conveniently this reduction is carried out with silanes such as, for example, phenylsilanes, trichlorosilane, hexachlorodisilane and the like. As solvents there can be used inert organic solvents such as, for example, aromatic hydrocarbons (e.g. benzene, toluene and the like), halogenated hydrocarbons (e.g. chloroform, dichloromethane) or acetonitrile and the like. In certain cases the reduction can also be carried out in the absence of solvents, for example when phenylsilanes are used. The reduction is conveniently carried out at an elevated temperature and preferably at the reflux temperature of the reaction mixture. The pressure is not critical and this reduction can accordingly be carried out readily at atmospheric pressure and, if desired, also at elevated pressure.

The resolution of a compound of formula I can be carried out in a manner known per se. It is conveniently carried out, for example, by complex formation with di-μ-chloro-bis[(R)-2-(1-(dimethylamino)ethyl)phenyl-C,N]-dipalladium (II) or with di-μ-chloro-bis[(S)-2-(1-(dimethylamino)ethyl)phenyl)-C,N]-dipalladium (II), separation of the two diastereomeric complexes by fractional crystallization and subsequent reductive liberation of the corresponding antipodes. The resolution can also be carried out by salt formation with formaldehyde in the presence of an optically active acid such as, for example, camphorsulphonic acid, crystallization and subsequent liberation of the corresponding antipode with base.

The compounds of formulae III and IV used as starting materials are known compounds or analogues of known compounds which can be prepared readily in a manner known per se.

The racemic compounds of formula II are also known compounds or analogues of known compounds which can be prepared in a manner known per se. The corresponding optically active compounds of formula II are, however, novel and also form an object of the present invention.

The novel optically active compounds of formula II can be prepared, for example, starting from compounds of the formula

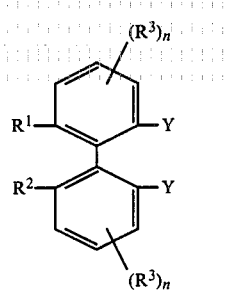

wherein R¹, R², R³ and n are defined as above.

The racemic compounds of formula VI can be resolved into the optical antipodes in a manner known per se. This is carried out, for example, by salt formation with optically active acids such as, for example, tartaric acid and subsequent separation by fractional crystallization. The thus-obtained optically active compounds of formula VI can then, just as the corresponding racemates, be converted in a manner known per se into the corresponding racemic or optically active compounds of formula II. This can be carried out, for example, by converting a racemic or optically active compound of formula VI by diazotization and Sandmeyer reaction or by reaction with an alkali metal iodide into a compound of the formula

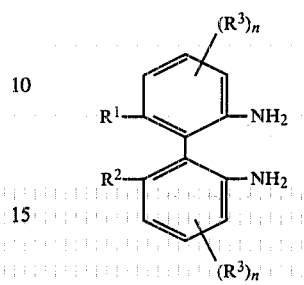

wherein R¹, R², R³ and n are defined as above and Y is chlorine, bromine or iodine, and subsequently converting this compound into a compound of formula II, for example by treatment with an alkyl lithium such as, for example, tert.-butyl lithium or with metallic lithium.

The racemate resolution required for the preparation of optically active compounds of formula II can also be carried out with compounds of the formula

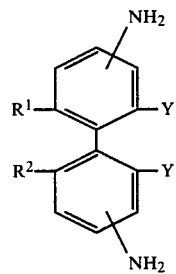

wherein $R^1$, $R^2$ and Y are defined above, in a manner analogous to the resolution of compounds of formula VI. After carrying out the resolution, the amino groups can then, for example, be alkylated to give compounds of formula VII in which n is the integer 1 and $R^3$ is di-lower alkylamino. Further, they can also be diazotized and then reduced to give compounds of formula VII in which n is the integer 0, or they can be diazotized and subsequently converted into compounds of formula VII in which n is the integer 1 and $R^3$ is fluorine, according to the method of Schiemann.

The compounds of formula II in which $R^1$ and $R^2$ are protected hydroxymethyl or $R^1$ and $R^2$ together are the group

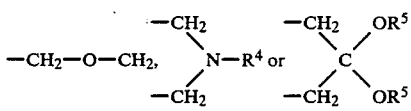

in which $R^4$ and $R^5$ are defined as above can also be prepared according to the following Reaction Scheme in which $R^6$ is hydrogen or lower alkyl.

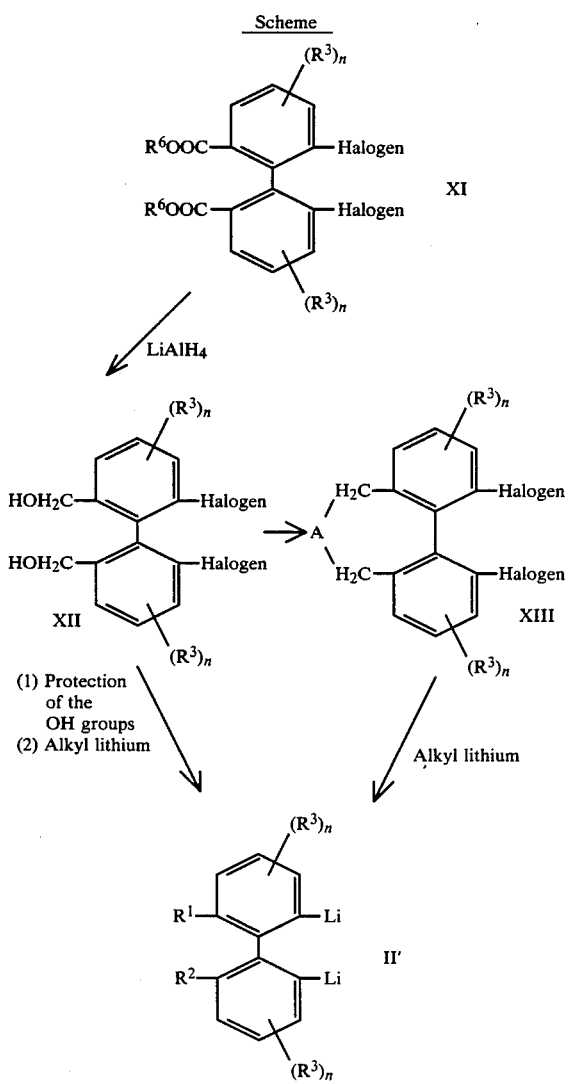

In the compounds of formula XIII A is oxygen $>NR^4$ or

in which $R^4$ and $R^5$ are defined as above.

The phosphorus compounds of formula I in accordance with the invention form complexes with metals of Group VIII, especially with rhodium, iridium and cobalt, which can be used as catalysts in asymmetric hydrogenations and for enantioselective hydrogen displacements in prochiral allylic systems. Rhodium is especially preferred. These catalysts, i.e. the complexes of a metal of Group VIII and the phosphorus compounds of formula I, are novel and are also an object of the present invention. These catalysts can be manufactured in a manner which is simple and known per se; for example, by reacting a compound of formula I with a compound which can yield a metal of Group VIII in a suitable inert organic or aqueous solvent. Compounds which can yield a metal of Group VIII are known. Suitable compounds which yield rhodium are, for example, rhodium trichloride hydrate, rhodium tribromide hydrate, rhodium sulphate or organic rhodium complexes with ethylene, propylene and the like, as well as with bis-olefins, for example 1,5-cyclooctadiene, 1,5-hexadiene, bicyclo[2.2.1]hepta-2,5-diene or with other dienes which form readily soluble complexes with rhodium. Preferred compounds which yield rhodium are, for example, di-μ-chloro-bis[η⁴-1,5-cyclooctadiene]dirhodium (I) or di-μ-chloro-bis[η⁴-norbornadiene]dirhodium (I).

Suitable compounds which yield one of the other metals of Group VIII are, for example, iridium trichloride hydrate, di-μ-chloro-bis-[η⁴-1,5-cyclooctadiene]-diiridium (I); cobalt dichloride, cobalt (II) acetate or naphthenate, cobalt (II) or cobalt (III) acetylacetonate and the like.

As mentioned above, the foregoing examples of phosphorus compounds of formula I and metals of Group VIII can be used as catalysts in asymmetric hydrogenations, for example in the asymmetric hydrogenation of compounds of the α-(acylamino)-acrylic acid type such as, for example, 2-(acetylamino)-3-(4-acetyloxy-3-methoxyphenyl)-2-propenoic acid.

Furthermore, the aforementioned catalysts can be used for enantioselective hydrogen displacements in prochiral allylic systems. They are particularly interesting, for example, in connection with the manufacture of optically active compounds of the formula

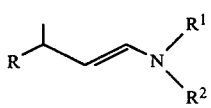

IX wherein R is protected hydroxymethyl or a group of the formula

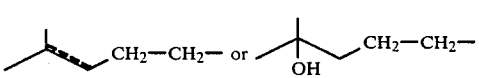

wherein the dotted lines can represent an additional bond and $R^1$ and $R^2$ are lower alkyl (1–7 C-atoms), starting from compounds of the formula

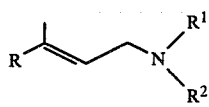 X wherein R, $R^1$ and $R^2$ are defined as above.

The compounds of formula IX, or the aldehydes obtained therefrom by hydrolysis, as well as the acids and alcohols derived from the latter are, for example, of interest as intermediates in the synthesis of the side chains of vitamins E and $K_1$.

For the performance of the aforementioned asymmetric hydrogenations and of the aforementioned hydrogen displacements, the phosphorus compounds of formula I can be brought into contact as such, in a solution of a compound to be treated, with a compound which yields a metal of Group VIII. Alternatively, the phosphorus compounds of formula I can be firstly reacted in a suitable solvent with a compound which yields a metal of Group VIII to give the corresponding catalyst complex and this can then be added to a solution of the compound to be treated. The latter method is preferred.

Not only the reaction of the phosphorus compounds of formula I with a compound which yields a metal of Group VIII, but also the aforementioned asymmetric hydrogenations and hydrogen displacements can be carried out in suitable organic solvents which are inert under the reaction conditions. Especially suitable organic solvents are lower alkanols such as, for example, methanol or ethanol, aromatic hydrocarbons such as benzene or toluene, cyclic ethers such as tetrahydrofuran or dioxan, esters such as, for example, ethyl acetate or mixtures thereof and the like. Furthermore, the complex formations can also be carried out in aqueous medium or in dichloromethane.

The ratio between the metal of Group VIII and the ligands of formula I conveniently lies between about 0.05 mol and about 5 mol, preferably between 0.5 mol and about 2 mol of metal per mol of ligand of formula I.

The amount of metal in the complexes with the ligands of formula I based on the compounds to be treated conveniently lies between about 0.01 mol % and about 2 mol %, preferably between about 0.05 mol % and about 1 mol % and especially between about 0.1 mol % and about 0.5 mol %.

The asymmetric hydrogenations using metal complexes with the ligands of formula I can conveniently be carried out at temperatures from about 20° C. to about 100° C., preferably from about 40° C. to about 90° C. These hydrogenations are conveniently carried out under pressure, especially under a pressure of about 1 to 100 bar, preferably 2 to 50 bar.

The aforementioned hydrogen displacements using metal complexes with the ligands of formula I can conveniently be carried out in an inert organic solvent and at a temperature from about room temperature to about 130° C. This reaction is preferably carried out at an elevated temperature, i.e. depending on the solvent used either at the reflux temperature of the reaction mixture or in a closed vessel under pressure.

The following Examples illustrate the present invention:

EXAMPLE 1

680 mg (2 mmol) of (RS)-2,2'-dibromo-6,6'-dimethyl-biphenyl were placed under argon gasification in a 100 ml sulphonation flask provided with a dropping funnel, thermometer, rubber septum cap and magnetic stirrer and 20 ml of absolute diethyl ether were injected in using a syringe. The resulting solution was cooled to about −90° to −100° C. and at this temperature was treated dropwise with 5.6 ml of an about 1.4M tert.butyl lithium solution in pentane (8 mmol). The solution was stirred at about −100° C. for a further 20 minutes, whereby it slowly became whitish turbid. A solution of 880 mg (4 mmol) of chlorodiphenylphosphine in 5 ml of absolute diethyl ether was then introduced dropwise at about −90° to −100° C. within 15 minutes. The mixture was left to warm to room temperature during 2 hours, the separation of a white precipitate setting in at about −60° C., and was stirred at room temperature for a further 1 hour. For the working-up, the mixture was treated under argon with water and dichloromethane, the organic phase was separated, washed with water and dried by filtration over sodium sulphate. The crystalline residue obtained after evaporation was recrystallized from ethyl acetate and there were obtained 620 mg of (RS)-(6,6'-dimethyl-2,2'-biphenylylene)-bis(diphenylphosphine) as white crystals with a melting point of 242°–243° C. From the mother liquor there were obtained after crystallization from ethanol/toluene a further 84 mg of product with a melting point of 240°–242° C.; total yield 704 mg.

The (RS)-2,2'-dibromo-6,6'-dimethyl-biphenyl used as the starting material can be prepared as follows:

A solution of 2.77 g (40.1 mmol) of sodium nitrite in 5 ml of water was added dropwise at −5° to 0° C. within 2 hours to a solution of 4.24 g (20 mmol) of (RS)-6,6'-dimethyl-2,2'-biphenyldiamine in 12 ml of 48% aqueous hydrogen bromide solution. The ice-cold dark diazonium salt solution was transferred into a dropping funnel and added dropwise within 15 minutes to a hot (70°–75° C.) solution of 25 ml of a copper (I) bromide solution in 48% aqueous hydrogen bromide solution. In so doing, the diazonium salt solution was held at 0° C. by the occasional additions of ice. After completion of the dropwise addition, the mixture was boiled at reflux for a further 5 minutes. The cooled solution was then extracted three times with 100 ml of ether each time. The combined organic extracts were washed twice with 50 ml of 2N hydrochloric acid each time, twice with 50 ml of saturated sodium bicarbonate solution each time and three times with 50 ml of water each time and then dried over sodium sulphate. The product (6 g) obtained after filtration and evaporation consisted according to gas chromatography of a 8:23:59 mixture of 2-bromo-6,6'-dimethyl-biphenyl, 2-bromo-2'-hydroxy-6,6'-dimethyl-biphenyl and (RS)-2,2'-dibromo-6,6'-dimethyl-biphenyl. Chromatography on silica gel [hexane/ether (9:1)] yielded 3.5 g of a 12:87 mixture of 2-bromo-6,6'-dimethyl-biphenyl and (RS)-2,2'-dibromo-6,6'-dimethyl-biphenyl, from which by two-fold recrystallization from pentane there were finally obtained 1.3 g of pure (RS)-2,2'-dibromo-6,6'-dimethyl-biphenyl with a melting point of 111°–112° C.

The following compounds were manufactured in a manner analogous to the foregoing:

(RS)-(4,4',6,6'-tetramethyl-2,2'-biphenylylene)-bis(diphenylphosphine); m.p. 249°–251° C.

(RS)-(4,4'-bis(dimethylamino)-6,6'-dimethyl-2,2'-biphenylylene)-bis(diphenylphosphine); m.p. 217.5°–219° C.

EXAMPLE 2

A suspension of 2.49 g (4.52 mmol) of (RS)-(6,6'-dimethyl-2,2'-biphenylylene)-bis(diphenylphosphine) and 1.31 g (2.26 mmol) of di-$\mu$-chloro-bis[(R)-2-(1-(dimethylamino)ethyl)phenyl-C,N]-dipalladium (II) in 100 ml of methanol was stirred at room temperature under argon until a homogeneous solution had resulted (about 4 hours). Thereto there was added dropwise a solution of 0.95 g (9.04 mmol) of ammonium tetrafluoroborate in 63 ml of water, the separation of a yellowish precipitate setting in after the addition of about 20 ml. The resulting precipitate was filtered off, washed with methanol/water (1:1) and dried over phosphorus pentoxide at 0.2 Torr, whereupon 1.79 g of yellowish crystals were obtained. The filtrate was diluted with 50 ml of water and stirred until the resulting precipitation coagulated (1 hour). Filtration and drying yielded a further 1.84 g of yellowish crystals; total yield 3.63 g.

The combined crystal fractions were dissolved in 150 ml of dichloromethane/diethyl ether (1:2). By the slow dropwise addition of 50 ml of hexane there was obtained a precipitate, 1.5 g of yellowish crystals being obtained after filtration. This material was recrystallized a further twice from 10 ml of dichloromethane by the portionwise additions of 10 ml of diethyl ether four times. In this manner there were obtained 1.07 g of [(R)-2-[1-(dimethylamino)ethyl]phenyl-C,N][(R)-6,6'-dimethyl-2,2'-biphenylylene)-bis(diphenylphosphine)]-palladium (II) tetrafluoroborate with a melting point of 213°–216° C.; $[\alpha]_D^{20} = +301.4°$ (c=1% in CHCl$_3$).

1 g (1.12 mmol) of the previously prepared tetrafluoroborate were introduced in small portions within 30 minutes at room temperature into a suspension of 42.6 mg (1.12 mmol) of lithium aluminium hydride in 15 ml of absolute tetrahydrofuran. The resulting black reaction mixture was stirred for 1 hour. Thereafter, the reaction was interrupted by the addition of a few drops of saturated sodium chloride solution, the mixture was treated with active carbon and filtered over a bed of sodium sulphate and Celite, and rinsed four times with 10 ml of tetrahydrofuran each time. The black-brown residue resulting after evaporation of the filtrate was taken up in a small amount of dichloromethane and filtered over a short column of silica gel with dichloromethane. The yellow filtrate was evaporated and the crystalline residue was recrystallized from ethanol/toluene. There were obtained 121 mg of (R)-(6,6'-dimethyl-2,2'-biphenylylene)-bis(diphenylphosphine) as white crystals with a melting point of 210°–212.5° C.; $[\alpha]_D^{20} = -42.7°$ (c=1% in CHCl$_3$).

EXAMPLE 3

In a manner analogous to that described in Example 1, 5.1 g (15 mmol) of (R)-2,2'-dibromo-6,6'-dimethyl-diphenyl (m.p. 107.5°–109° C.; optical purity about 80%) were reacted with tert.butyl lithium and subsequently with chlorodiphenylphosphine. For the working-up, the mixture obtained was treated with 80 ml of dichloromethane, 60 ml of tetrahydrofuran and 50 ml of water and warmed briefly in order to bring all of the precipitate into solution. The aqueous phase was removed by means of a cannula and the organic phase was washed twice with 50 ml of water each time. Subsequently, the solvent was evaporated and the residue was recrystallized from 210 ml of ethyl acetate. After 2 days, 1.62 g of racemic (RS)-(6,6'-dimethyl-2,2'-biphenylylene)-bis(diphenylphosphine) were filtered off. The filtrate was evaporated and the residue (7.9 g) was recrystallized from a mixture of 50 ml of ethanol and 25 ml of toluene. In this manner there were obtained 3.43 g of optically active (R)-(6,6'-dimethyl-2,2'-biphenylylene)-bis(diphenylphosphine) with a melting point of 212°–213° C.; $[\alpha]_D^{20} = -42°$ (c=1% in CHCl$_3$). From the mother liquor there was obtained a further 0.61 g of product of melting point 209°–210.5° C.; $[\alpha]_D^{20} = -39.9°$ (c=1% in CHCl$_3$); total yield 4.04 g.

The optically active (R)-2,2'-dibromo-6,6'-dimethyl-biphenyl used as the starting material was prepared from (R)-6,6'-dimethyl-2,2'-biphenyldiamine in a manner analogous to that described in Example 1.

EXAMPLE 4

In a manner analogous to that described in Example 3, from 5.1 g (15 mmol) of (S)-2,2'-dibromo-6,6'-dimethyl-biphenyl (m.p. 108.5°–109° C.; $[\alpha]_D^{25} = -11.7°$ (c=1% in ethanol); optical purity about 90%) there were obtained 4.25 g of optically active (S)-(6,6'-dimethyl-2,2'-biphenylylene)-bis(diphenylphosphine) with a melting point of 212°–213° C.; $[\alpha]_D^{20} = +41.7°$ (c=1% in CHCl$_3$). From the mother liquor there was obtained a further 0.40 g of product with a melting point of 213°–214° C.; $[\alpha]_D^{20} = +41.4°$ (c=1% in CHCl$_3$). Total yield 4.65 g.

The (S)-2,2'-dibromo-6,6'-dimethyl-biphenyl used as the starting material was prepared from (S)-6,6'-dimethyl-2,2'-biphenyldiamine in a manner analogous to that described in Example 1.

EXAMPLE 5

11.0 g (20 mmol) of (RS)-(4,4',6,6'-tetramethyl-2,2'-biphenylylene)-bis(diphenylphosphine) (manufactured in a manner analogous to that described in Example 1) and 5.80 g (10 mmol) of di-$\mu$-chloro-bis[(R)-2-(1-(dimethylamino)ethyl)phenyl-C,N]dipalladium (II) were placed in a 0.1 l sulphonation flask provided with a dropping funnel, magnetic stirrer and argon gasification and treated with 200 ml of deoxygenated methanol using an injection syringe. The suspension was stirred at room temperature overnight, after which time a clear solution was obtained. Thereto there was now added dropwise within 1 hour a solution of 1.16 g (11 mmol) of ammonium tetrafluoroborate in 50 ml of deoxygenated water, the separation of a precipitate occurring after the addition of about half of the solution. After stirring for a further 3 hours, the mixture was filtered, the filter residue was washed with 20 ml of methanol/water (4:1) and dried in a high vacuum, there being obtained 6.86 g of [(R)-2-(1-(dimethylamino)ethyl)phenyl-C,N][(R)-(4,4',6,6'-tetramethyl-2-biphenylylene)-bis(diphenylphosphine)]palladium (II) tetrafluoroborate in the form of a yellowish powder; m.p. 190°–193° C. (decomposition); $[\alpha]_D^{20} = +286.0°$ (c=1.16% in CHCl$_3$).

A solution of 1.16 g (11 mmol) of ammonium tetrafluoroborate in 50 ml of water was added dropwise to the filtrate obtained above and the separated crystallizate was filtered off after stirring for 1 hour, washed with 20 ml of methanol/water (2:1) and dried in the high vacuum. There were thus obtained 9.6 g of a yellowish powder. An additional 0.92 g of a yellowish powder was obtained by treating the second filtrate with 200 ml of water. The latter two crystal fractions were combined and recrystallized from a mixture of 40 ml of dichloromethane and 100 ml of ether. There were obtained 5.54 g of [(R)-2-(1-(dimethylamino)ethyl)phenyl-C,N][(S)-(4,4',6,6'-tetramethyl-2,2'-biphenylylene)-bis(diphenylphosphine)]palladium (II) tetrafluoroborate as yellowish crystals; m.p. 198°–200° C. (decomposition); $[\alpha]_D^{20} = -298°$ (c=1.19% in CHCl$_3$).

A solution of 6.30 g (6.85 mmol) of [(R)-2-[1-(dimethylamino)ethyl]phenyl-C,N][(R)-(4,4',6,6'-tetramethyl-2,2'-biphenylylene)-bis(diphenylphosphine)]palladium (II) tetrafluoroborate in 85 ml of acetone was placed under argon, then treated with 17 ml of 10M hydrochloric acid, heated and boiled under reflux for 60 minutes. 300 ml of water were then slowly added dropwise to the still warm yellow solution while stirring well. The resulting suspension was stirred for a further 30 minutes. The precipitate was filtered off, washed twice with water and dried in a high vacuum, there being obtained 5.62 g of crude dichloro-[(R)-(4,4',6,6'-tetramethyl-2,2'-biphenylylene)-bis(diphenylphosphine)]palladium (II) as a yellow powder.

A solution of 5.57 g of the substance obtained according to the preceding paragraph in 100 ml of dichloromethane was treated with 40 ml of water, the mixture was placed under argon and then treated in one portion with 5.3 g (81 mmol) of potassium cyanide. The two-phase system was vigorously stirred for 30 minutes, then the dichloromethane phase was separated and the aqueous solution was extracted once with dichloromethane. The combined organic solutions were washed with water and saturated sodium chloride solution, dried over sodium sulphate, filtered and evaporated. The yellow crystalline residue was taken up in 15 ml of toluene and the solution was treated with active carbon, filtered over Celite and again evaporated. Recrystallization of the residue from ethanol/toluene yielded 2.70 g of (R)-(4,4'-6,6'-tetramethyl-2,2'-biphenylylene)-bis(diphenylphosphine) as white crystals of melting point 217°–218° C.; $[\alpha]_D^{20} = -21.5°$ (c=1.03% in CHCl$_3$). An additional 0.5 g of substance of melting point 215.5°–218° C. was isolated from the mother liquor; the total yield thus amounted to 3.2 g.

The liberation of the corresponding (S)-(4,4',6,6'-tetramethyl-2,2'-biphenylylene)-bis(diphenylphosphine) was carried out in an analogous manner and there was obtained a product having a melting point of 217.5°–219° C.; $[\alpha]_D^{20} = +21.4°$ (c=1.11% in CHCl$_3$).

The following compounds were manufactured in a manner analogous to the foregoing, but with liberation of the phosphine with lithium aluminium hydride as described in Example 2.

(R)-(4,4'-bis(dimethylamino)-6,6'-dimethyl-2,2'-biphenylylene)-bis(diphenylphosphine); m.p. 184°–185° C.; $[\alpha]_D^{20} = +25.4°$ (c=1% in CHCl$_3$).
(S)-4,4'-bis(dimethylamino)-6,6'-dimethyl-2,2'-biphenylylene)-bis(diphenylphosphine); m.p. 184°–185° C.; $[\alpha]_D^{20} = -26.3$ (c=1% in CHCl$_3$).

EXAMPLE 6

275 mg (0.5 mmol) of (R)-(6,6'-dimethyl-2,2'-biphenylylene)-bis(diphenylphosphine) and 115 mg (0.25 mmol) of di-μ-chloro-bis[η$^4$-bicyclo[2.2.1]hepta-2,5-diene]-dirhodium (I) were placed under argon in a Schlenk tube and treated with 4 ml of deoxygenated methanol. The mixture was stirred until a homogeneous red solution had resulted (1.5 hours). Thereto there was now added dropwise within 45 minutes a solution of 61 mg (0.55 mmol) of sodium tetrafluoroborate in 1.1 ml of deoxygenated water, an orange precipitate resulting.

After stirring for a further 1 hour, the mixture was filtered under argon, the filter residue was washed twice with 0.5 ml of water each time and dried in a high vacuum. There were obtained 360 mg of [η$^4$-bicyclo[2.2.1]-hepta-2,5-diene][(R)-(6,6'-dimethyl-2-2'-biphenylylene)-bis(diphenylphosphine)]rhodium (I) tetrafluoroborate as orange microcrystals with $[\alpha]_D^{20} = -35.9°$ (c=0.445% in CHCl$_3$).

In a manner analogous to the foregoing, from 1.10 g (2 mmol) of (S)-(6,6'-dimethyl-2,2'-biphenylylene)-bis(diphenylphosphine) there were obtained 1.52 g of [η$^4$-bicyclo[2.2.1]hepta-2,5-diene][(S)-(6,6'-dimethyl-2,2'-biphenylylene)-bis(diphenylphosphine)]rhodium (I) tetrafluoroborate; $[\alpha]_D^{20} = +31.95°$ (c=0.482% in CHCl$_3$). Recrystallization from deoxygenated methanol yielded 1.11 g of this substance as deep red crystals with $[\alpha]_D^{20} = +34°$ (c=0.54% in CHCl$_3$).

EXAMPLE 7

The following compounds were manufactured in a manner analogous to that described by R. R. Schrock et al, J.A.C.S., 93, 3089 (1971):

[η$^4$-1,5-Cyclooctadiene][(R)-6,6'-dimethyl-2,2'-biphenylylene)-bis(diphenylphosphine)]rhodium (I) perchlorate. Mutarotation was observed in the rotation determinations in dichloromethane and in acetonitrile.

[η$^4$-1,5-Cyclooctadiene][(S)-(6,6'-dimethyl-2,2'-biphenylylene)-bis(diphenylphosphine)]rhodium (I) perchlorate. Mutarotation was observed in the rotation determination in chloroform.

$[\alpha]_D^{20}$ (about 1 min.) = +20.5° (c=0.464% in CHCl$_3$)

$[\alpha]_D^{20}$ (about 5 min.) = −26.9° (c=0.464% in CHCL$_3$)

EXAMPLE 8

1.14 g (5.0 mmol) of (Z)-N,N-diethyl-3,7-dimethyl-2,6-octadienylamine, 5 ml of tetrahydrofuran and 16 mg (0.0192 mmol) of [η$^4$-bicyclo[2.2.1]hepta-2,5-diene][(R)-(6,6'-dimethyl-2,2'-biphenylylene)-bis(diphenylphosphine)]rhodium (I) tetrafluoroborate were placed in a Pyrex bomb tube under nitrogen. After degasifying the mixture, the tube was sealed and heated in a bomb tube oven at 85° C. to 90° C. for 19 hours. The brownish-red mixture was evaporated and the residue was distilled in a bulb-tube at about 120° C./0.05 mmHg. There were obtained 1.09 g of (1E,3R)-N,N-diethyl-3,7-dimethyl-1,6-octadienylamine as a colourless distillate.

The colourless distillate obtained was subsequently treated at 0° C. with 8 ml of 50% acetic acid, the mixture was stirred vigorously for 10 minutes, covered with pentane and stirred for a further 30 minutes. For the working-up, the phases were separated and the aqueous phase was extracted twice with pentane. The combined organic extracts were washed once with 0.2N sulphuric acid, once with water and once with saturated sodium chloride solution, dried over sodium sulphate, filtered and evaporated. After bulb-tube distillation of the residue at about 120° C./15 mmHg, there were obtained 0.72 g of (R)-citronellal having a purity of 93.5% according to gas chromatography. A sample of this material was purified further by chromatography on SiO$_2$ (hexane/4% ethyl acetate); $[\alpha]_D^{20} = +19.3°$ (c=5% in CHCl$_3$). The enantiomeric purity (ee) was determined in analogy to the method of D. Valentine, Jr., et al., J. Org. Chem. 41, 62 (1976) by oxidation to the acid, amide formation with (R)-α-methyl-4-nitrobenzylamine and analysis of the diastereomeric amides by means of gas chromatography or liquid chromatography. There was thus found a RR/SR-diastereomer ratio of 99.2:0.8 and 99.0:1.0, respectively, from which a value of 98% ee was derived for the enantiomeric purity.

EXAMPLE 9

(Z)-N,N-diethyl-3,7-dimethyl-2,6-octadienylamine was isomerized with [η⁴-bicyclo[2.2.1]hepta-2,5-diene][(S)-(6,6'-dimethyl-2,2'-biphenylylene)-bis(diphenylphosphine)]rhodium (I) tetrafluoroborate in a manner analogous to that described in Example 8. The hydrolysis of the enamine obtained to (S)-citronellal and the determination of the enantiomeric purity were also carried out in a manner analogous to that described in Example 8. The enantiomeric purity amounted to 99% ee.

EXAMPLE 10

In a manner analogous to that described in Example 8, (E)-N,N-diethyl-4-benzyloxy-3-methyl-2-butenylamine was isomerized (reaction temperature 85° C.) with [η⁴-1,5-cyclooctadiene][(S)-(6,6'-dimethyl-2,2'-biphenylylene)-bis(diphenylphosphine)]rhodium (I) perchlorate to give (1E,3S)-N,N-diethyl-4-benzyloxy-3-methyl-1-butenylamine and this was hydrolyzed to (S)-4-benzyloxy-3-methylbutanal. The enantiomeric purity was ascertained as 98.8% ee.

EXAMPLE 11

In a manner analogous to that described in Example 8, (E)-N,N-diethyl-4-benzyloxy-3-methyl-2-butenylamine was isomerized (reaction temperature 75° C.) with [η⁴-1,5-cyclooctadiene][(R)-(6,6'-dimethyl-2,2'-biphenylylene)-bis(diphenylphosphine)]rhodium (I) perchlorate to give (1E,3R)-N,N-diethyl-4-benzyloxy-3-methyl-1-butenylamine and this was hydrolyzed to (R)-4-benzyloxy-3-methylbutanal. The enantiomeric purity was ascertained as 99.2% ee.

We claim:

1. Chiral phosphorus compounds of either the (R)- or the (S)-form, of the formula

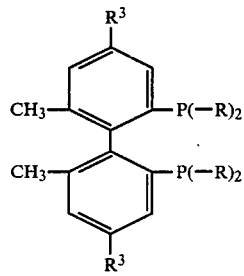

wherein R is phenyl or phenyl substituted with lower alkyl, lower alkoxy, di-lower alkylamino or fluorine, and $R^3$ is di-lower alkylamino.

2. Phosphorus compounds according to claim 1 wherein R is phenyl substituted with methyl or fluorine and $R^3$ is dimethylamino.

3. In accordance with claim 1, the compound (S)-(4,4'-bis-(dimethylamino)-6,6'-dimethyl-2,2'-biphenylylene-bis(diphenylphosphine).

4. In accordance with claim 1, the compound (R)-(4,4'-bis-(dimethylamino)-6,6'-dimethyl-2,2'-biphenylylene)-bis(diphenylphosphine).

* * * * *